United States Patent
Björn et al.

(10) Patent No.: US 6,280,194 B1
(45) Date of Patent: Aug. 28, 2001

(54) ARRANGEMENT AND ITS USE FOR ANCHORING A THREADED IMPLANT IN BONE, FOR EXAMPLE DENTINE

(75) Inventors: Göran Björn, Onsala (SE); Bjarne Kvarnström, Westmont, IL (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/530,483

(22) PCT Filed: Oct. 29, 1998

(86) PCT No.: PCT/SE98/01957

§ 371 Date: Jun. 26, 2000

§ 102(e) Date: Jun. 26, 2000

(87) PCT Pub. No.: WO99/23970

PCT Pub. Date: May 20, 1999

(30) Foreign Application Priority Data

Nov. 11, 1997 (SE) .................................................. 9704113

(51) Int. Cl.[7] .................................................. A61C 8/00
(52) U.S. Cl. .................................................. 433/174
(58) Field of Search .................................. 433/172, 173, 433/174, 175, 176, 201.1

(56) References Cited

U.S. PATENT DOCUMENTS

| | | | |
|---|---|---|---|
| 5,350,301 | * 9/1994 | DeBuck | 433/173 |
| 5,362,235 | * 11/1994 | Daftary | 433/172 |
| 5,362,236 | 11/1994 | Branemark . | |
| 5,564,926 | 10/1996 | Brånemark . | |

FOREIGN PATENT DOCUMENTS

WO 96/18355  6/1996  (WO) .

* cited by examiner

*Primary Examiner*—Nicholas D. Lucchesi
(74) *Attorney, Agent, or Firm*—Connolly Bove Lodge & Hutz

(57) ABSTRACT

In an arrangement for anchoring a threaded implant (1) in jawbone (2) by means of a screwing instrument (6), use is made of an implant which, at its upper part, is provided with an anchoring hole (1c) for a screw (5) intended to secure an element or fixture holder (4) that can be attached to the implant. The centre axis of the anchoring hole is inclined in relation to the longitudinal axis (1b) of the implant. The element is provided with means (4d) for cooperation with the instrument (6). The element and its means of cooperation permit application of the instrument in a way which ensures that the axis of rotation (6d) of the instrument essentially coincides with a continuation of the longitudinal axis (1b) of the implant.

11 Claims, 2 Drawing Sheets

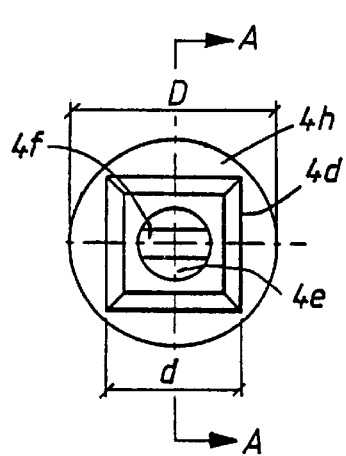
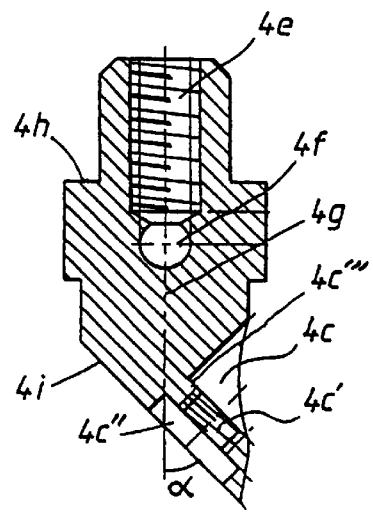
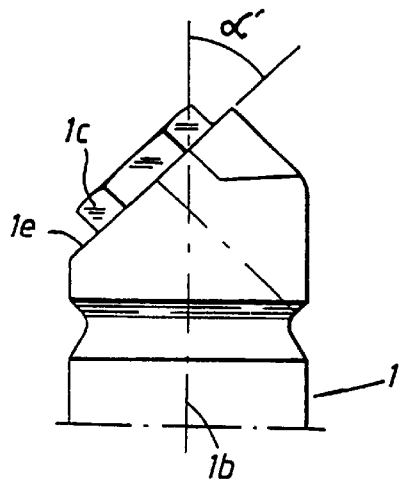
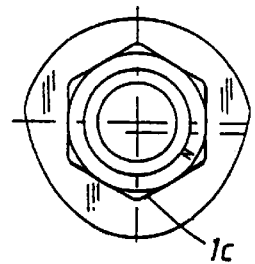

ARRANGEMENT AND ITS USE FOR ANCHORING A THREADED IMPLANT IN BONE, FOR EXAMPLE DENTINE

TECHNICAL FIELD

The present invention relates to an arrangement permitting anchoring of a threaded implant in bone, for example jawbone, in the human body by means of a screwing/tightening instrument. At its upper part, the implant has an anchoring hole for a unit, preferably in the form of a screw, intended to secure an element that can be attached to the implant and can in this case consist of a fixture holder, fixture, spacer, etc. The centre axis of the anchoring hole is also inclined in relation to the longitudinal axis of the implant.

The invention also relates to the use of an element, for example in the form of a fixture holder, fixture, spacer, etc., which can be attached to a threaded implant, where the implant is screwed into a bone, for example the jawbone, by means of an instrument and where the implant has an anchoring hole for the securing unit, preferably in the form of a screw, for the element in question.

PRIOR ART

The invention is further concerned with the screwing functions of implants of the type described, inter alia, in Swedish Patent 9203563-3 and PCT application WO 96/18355. A characteristic of this type of implant is the presence of an inclined threaded hole which can be arranged in a fixture for the implant or in the actual implant itself. The centre axis of the hole is inclined in relation to the axis of rotation of the implant. When anchoring further fixtures, spacers, etc. in the implant, an anchoring screw is used which can be screwed tightly into the internal thread of the anchoring hole.

The said PCT document mentions the possibility of using screwing instruments which are connected to the upper parts of the implant for the purpose of screwing the implant tightly into the bone in question.

DESCRIPTION OF THE INVENTION

TECHNICAL PROBLEM

A reliable and as far as possible simplified tightening function needs to be found. The invention is intended to solve this problem, among others.

The said PCT document proposes an instrument which uses the anchoring screw for securing a fixture to the implant. The instrument is provided with an inclined recess which coincides with or constitutes a continuation of the anchoring hole. The anchoring screw is in this case removed first, and the instrument is applied in such a way that the recess of the instrument is arranged concentrically in relation to the recess in the implant, after which they can be screwed tight by means of the said anchoring screw. When the implant has been tightened, the anchoring screw is loosened and removed, after which the instrument can also be removed. This procedure is a lengthy one. The inclined recess in the instrument is deep and problems can occur during screwing, unscrewing, etc., of the anchoring screw in question. The present invention is intended to solve this problem too.

It may be desirable not to have to act on the anchoring screw during the tightening or screwing-in of the implant into the bone. The invention solves this problem too.

SOLUTION

The feature which can principally be regarded as characterizing an arrangement according to the invention is, inter alia, that the element (fixture holder, fixture, etc.) that can be attached by means of the said unit (screw) is provided with means of cooperation with the instrument, and that the element and its means of cooperation are arranged to permit application of the instrument in a way which ensures that the axis of rotation of the instrument essentially coincides with the continuation of the axis of rotation of the implant.

An arrangement according to the invention can principally be regarded as being characterized by the fact that the tightening function exerted by means of the instrument is separate from the securing function exerted by means of the unit (screw) by virtue of the fact that the element (fixture holder, fixture, spacer, etc.) has a first portion via which the element is anchored by the anchoring unit in the implant, and a second portion which is separate from the first portion and which has cooperating means for the instrument.

Embodiments of the arrangement are specified in the attached subclaims.

The use according to the invention can principally be regarded as being characterized by the fact that the element (fixture holder, fixture, spacer, etc.) is used in the tightening operation with the instrument by virtue of the fact that the element has means cooperating with the instrument, to which means the instrument is applied with its axis of rotation essentially coinciding with the continuation of the axis of rotation of the implant.

Further developments of the said use are specified in the attached subclaims.

ADVANTAGES

By means of what has been proposed above, a considerably simplified and less expensive tightening function is obtained for implants in jawbone. The handling of small tightening screws can be avoided, and simple application to the implant for turning it or screwing it in can be effected. The locking function for the instrument can be made extremely simple by the fact that a conventional locking screw can be used in a manner known per se. The implant with associated element, i.e. fixture holder, fixture, spacer, etc., can be supplied as one unit to which the tightening instrument can be applied in an extremely simple and effective manner.

DESCRIPTION OF THE FIGURES

A presently proposed embodiment of an arrangement and use having the significant characteristics of the invention will be described below with reference to the attached drawings, in which:

FIG. 3 is a plan view of means which are arranged on the upper part of the fixture holder and can cooperate with the instrument, FIG. 4 shows, in vertical section along the line A—A, the design of the fixture holder, FIG. 5 shows, obliquely from above, the design of a nut-shaped part on the implant, and FIG. 6 shows the upper parts of the implant from the side, with the associated nut-shaped part according to FIG. 5.

DETAILED EMBODIMENT

Figure 1:
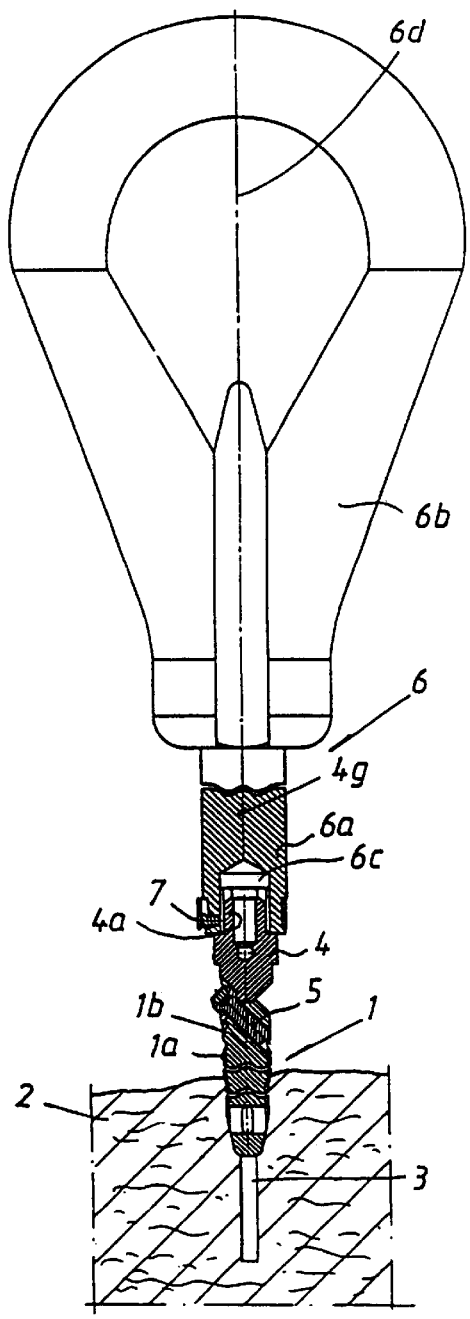
FIG. 1 shows, in a vertical view and partial cross section, an implant which has been partially screwed into jawbone by means of an instrument (screwing instrument)
Figure 2:
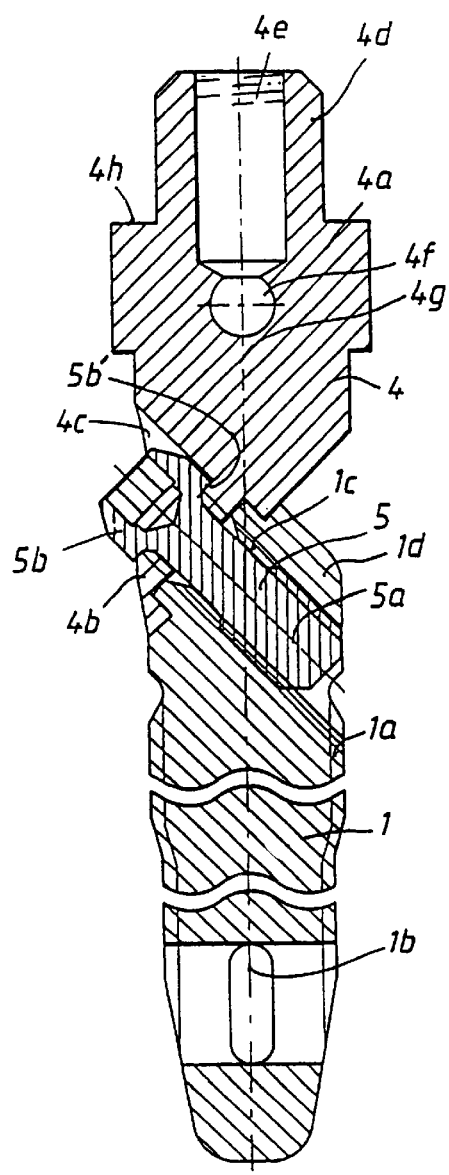
FIG. 2 shows, in a vertical section, and enlarged in relation to FIG. 1, the implant together with a fixture holder screwed into the latter.

In FIGS. 1 and 2, an implant is indicated by 1. The implant is intended to be screwed into jawbone 2, and it can be screwed into a pre-drilled hole 3. The implant can be of the self-tapping type and is in this case provided with an external thread 1a. Attached to the upper parts of the implant there is an element 4, for example in the form of a fixture holder. This can be attached or applied by means of a screw 5 or other anchoring unit. An instrument, for example in the form of a screwing instrument 6 with shaft-like part 6a and handle part 6b, can be attached/applied to the upper parts or portion 4a of the element. The instrument is provided with a locking arrangement, for example in the form of a locking screw 7. The fixture holder 4 is provided with a second portion 4b which is separate from the first portion 4a.

The axis of rotation (longitudinal axis) of the implant is indicated by 1b, and the longitudinal axis or axis of rotation of the screw 5 is shown by 5a. The implant has an inclined, threaded recess 1c, in which the screw 5 can be screwed or the unit can be anchored. The centre axis of the hole coincides with the centre axis 5a of the screw. The centre axis of the hole slopes at an angle, for example an angle of about 45°, in relation to the longitudinal axis 1b of the implant. The said second portion 4b has a recess 4c which is concentric in relation to the recess 1c when the holder is in its secured position on the implant. The head 5b of the screw 5 is partially engaged in the recess 4c when the holder is in its secured position in the implant.

The upper portion 4a of the holder 4 is provided with a key grip 4d. The holder 4 is additionally provided with a central recess 4e (can be threaded) which opens at the top, and a transverse recess 4f in the bottom part of the recess. The centre line 4g of the holder coincides essentially with the axis of rotation 1b of the implant. The centre line of the hole 4e coincides with the centre line 4g of the holder 4. A shoulder portion of the holder is shown by 4h. The upper part of the implant is shown by 1d.

FIG. 3 shows a four-sided key grip for the instrument 6 which is provided with a corresponding internal four-wall recess 6c (FIG. 1). The key grip can have another number of sides, and the recess 6c likewise can have another number of corresponding walls. The part bearing the shoulder portion 4h can have a diameter of about 6 mm, and the external dimension d of the key grip can be about 3.9 mm.

FIG. 4 shows that the recess 4c passes into subsidiary recesses 4c' and 41c", of which 4c' is threaded. The diameter of the recess 4c' is less than the diameter of the recess 4c so as to form a shoulder 4c'" with which an underside 5b' (see FIG. 2) of the screw 5 cooperates or on which it bears when the screw is in the screwed-in position. The holder 4 has an inclined surface 4i which slopes at an angle α of about 45° in relation to the axis 4g.

FIGS. 5 and 6 show the outer shape of the implant which in this case comprises a hexagonal nut 1c to which the holder 4 can be fixed in rotation by means of the recess 4c' which is designed with an internal hexagon shape corresponding to the outer shape of 1c. Other numbers of edges can be used.

The method can in this case be that the holder is first anchored to the implant by the recess 4c" being brought over the nut shape 1c and the member 5 thereafter being applied and made fast (screwed). The instrument can thereafter be engaged on the four-edged shape 4d via its corresponding four-edged recess 6d, after which the locking member 7 is activated (the locking nut is tightened). When the implant is screwed fully into the jawbone 2, the locking member 7 is deactivated and the instrument 6 is removed from the holder 4, which in this way can be left in place, i.e. the unit or the screw 5 does not need to be removed, screwed tight and once again removed in order finally to be screwed back again into the respective recess.

The new arrangement is thus characterized by the fact that the tightening function exerted by means of the instrument is separate from the securing function which is exerted by the said unit or screw 5. The said functions are attributable to different parts of the holder, spacer, fixture, etc., which parts are thus separate or distinct. One element, for example in the form of a holder according to the above, can in this case be used in the screwing function by means of the instrument, the instrument being applied in such a way that the instrument 6d coincides with the longitudinal axis 1b of the implant. Reference is made to FIG. 1 where it can be seen that the direction of the longitudinal axis 6d of the instrument coincides with the continuations of the longitudinal axes 1b and 4g, respectively, of the implant and of the fixture holder.

FIG. 6 shows an inclined surface of the implant indicated by 1e. This surface slopes in relation to the longitudinal axis 1b of the implant by an angle α' which essentially corresponds to the angle α in FIG. 4. The arrangement is also such that when the surfaces 4i and 1e bear against each other, the longitudinal axes 4g and 1b essentially coincide, which is also true of the longitudinal axis 6d of the instrument since the key grip 4d is arranged concentrically around the longitudinal axis 4g of the holder.

The invention is not limited to the embodiment shown above by way of example, but can be modified within the scope of the attached patent claims and the inventive concept.

What is claimed is:

1. A threaded implant, anchoring device, comprising:
   an implant having a threaded anchoring hole at an upper end for securing an element attached to said implant by a securing unit, the center axis of said anchoring hole being inclined in relation to the longitudinal axis of said implant; and
   a screwing instrument, wherein
      said element has a means for cooperating with said screwing instrument so that said screwing instrument rotates about the longitudinal axis formed by said implant.

2. The threaded implant, anchoring device according to claim 1, further comprising:
   a key grip arranged concentrically around the center axis of said element, at the upper end of said element, wherein
      the center longitudinal axis of said element essentially coincides with the longitudinal axis of said implant.

3. The threaded implant, anchoring device according to claim 2, wherein:
   said key grip has a plurality of edges; and
   said screwing instrument, at its part cooperating with said element, has a recess with straight wall parts, whereby the number of said plurality of edges corresponds to the number of said straight wall parts.

4. The threaded implant, anchoring device according to claim 1, wherein:
   said element has a first inclined surface that can be applied against a corresponding second inclined surface on said implant, where said element and said implant come into contact.

5. The threaded implant, anchoring device according to claim 1, wherein:
   said element has an attachment arranged rotationally fixed, relative to said implant, whereby
   said element, at its portion having said attachment, has an inclined recess that is concentric in relation to said anchoring hole and
   an outer part of said securing unit is partially engaged in said inclined recess.

6. The threaded implant, anchoring device according to claim 1, wherein:
   said screwing instrument has a locking arrangement for locking said screwing instrument to said cooperating means of said element.

7. The threaded implant, anchoring device according to claim 1, wherein:
   said screwing instrument has a shaft part and a handle part, whereby
   said shaft part, at a free end, supports a plurality of first members cooperating with said element and
   said handle supports an exerted rotational torque when said implant is screwed into place.

8. The threaded implant, anchoring device according to claim 1, wherein:
   said element has a flange with a threaded hole therethrough for securing a number of second members, and
   said element has a second hole arranged under the bottom of said threaded hole, in the transverse direction to said threaded hole.

9. A threaded implant, anchoring device, comprising:
   an implant having a threaded anchoring hole at an upper end for securing an element attached to said implant by a securing unit, the center axis of said anchoring hole being inclined in relation to the longitudinal axis of said implant; and
   a screwing instrument, wherein
      said element has a first portion anchored by said securing unit of said implant,
      said element has a second portion, separate from said first portion, cooperating with said screwing instrument.

10. A method of using an element to screw an implant into a bone, comprising the steps of:
    attaching an element to a threaded implant by means of an anchoring hole in said implant and a securing unit, wherein the center axis of said anchoring hole is inclined in relation to the axis of rotation of said implant;
    using the cooperation between said element and a screwing instrument to screw said implant into the bone;
    applying said instrument so that its axis of rotation essentially coincides with the axis of rotation of said implant; and
    screwing said implant into the bone.

11. The method of using an element to screw an implant into a bone according to claim 10, further comprising the step of:
    using said element to form a key grip for a corresponding key grip on said screwing instrument.

* * * * *